United States Patent [19]
Novack

[11] Patent Number: 5,112,352
[45] Date of Patent: May 12, 1992

[54] PECTORAL IMPLANT AND METHOD FOR IMPLANTING THE SAME

[76] Inventor: Brian Novack, 2131 Century Park La., #201, Los Angeles, Calif. 90067

[21] Appl. No.: 732,056

[22] Filed: Jul. 18, 1991

[51] Int. Cl.$^5$ .................................................. A61F 2/12
[52] U.S. Cl. .................................................. 623/8
[58] Field of Search .................................... 623/7, 8

[56] References Cited

U.S. PATENT DOCUMENTS

| | | | |
|---|---|---|---|
| 3,460,975 | 8/1969 | Stebleton | 623/11 |
| 3,986,213 | 10/1976 | Lynch | 623/8 |
| 4,095,295 | 6/1978 | Lake | 623/8 |
| 4,597,763 | 7/1986 | Schweikhart | 623/8 |
| 4,713,073 | 12/1987 | Reinmuller | 623/8 |
| 4,756,862 | 7/1988 | Spector | 623/11 |
| 4,790,849 | 12/1988 | Terino | 623/11 |
| 4,969,901 | 11/1990 | Binder | 623/11 |

OTHER PUBLICATIONS

Muscle & Fitness, Dec. 1986, Cover, pp. 94–98.

*Primary Examiner*—Randy C. Shay
*Attorney, Agent, or Firm*—Poms, Smith, Lande & Rose

[57] ABSTRACT

A pectoral implant is disclosed of a soft silicone material that is contoured to the chest of a male. The implant is split partway therethrough so that it can be folded and inserted into a small slit under the armpit of a male and moved into the chest area to simulate the built-up chest appearance of the male.

7 Claims, 2 Drawing Sheets

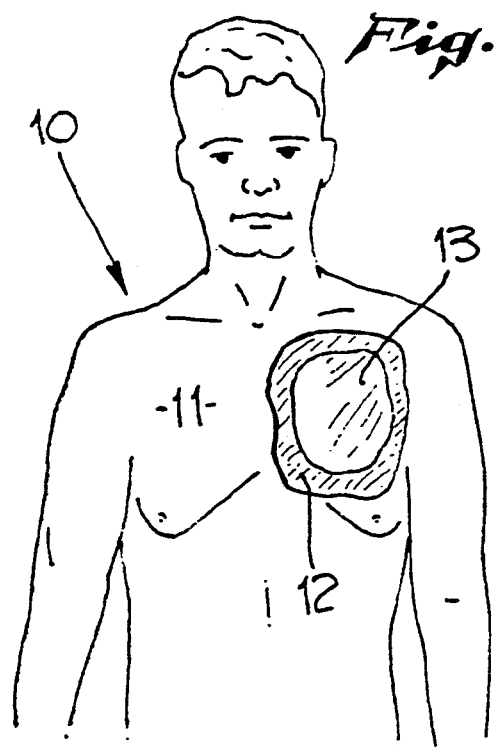
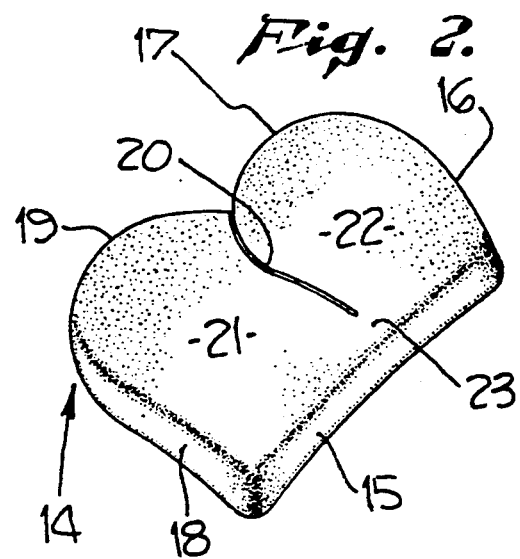
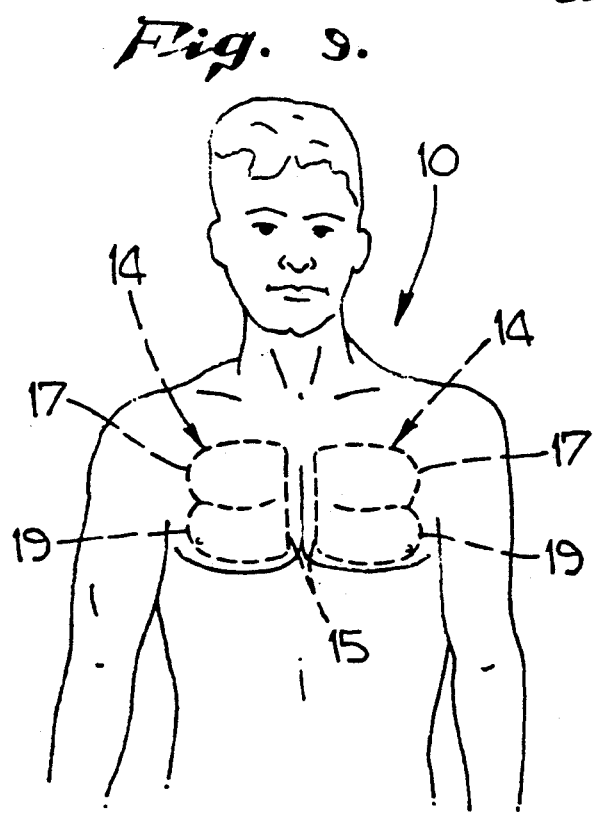
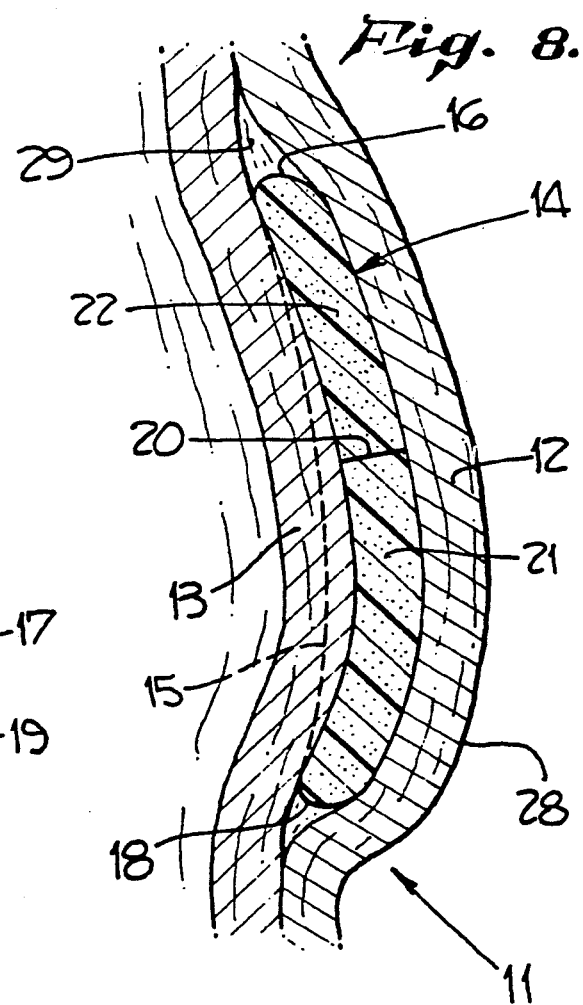

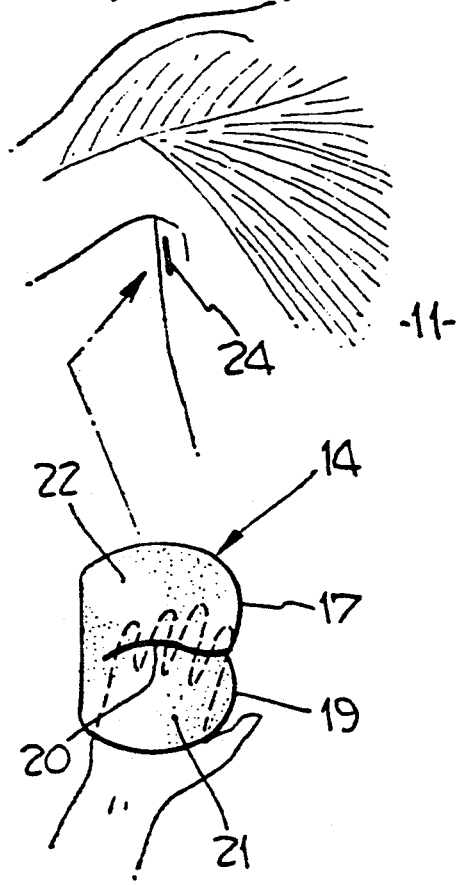
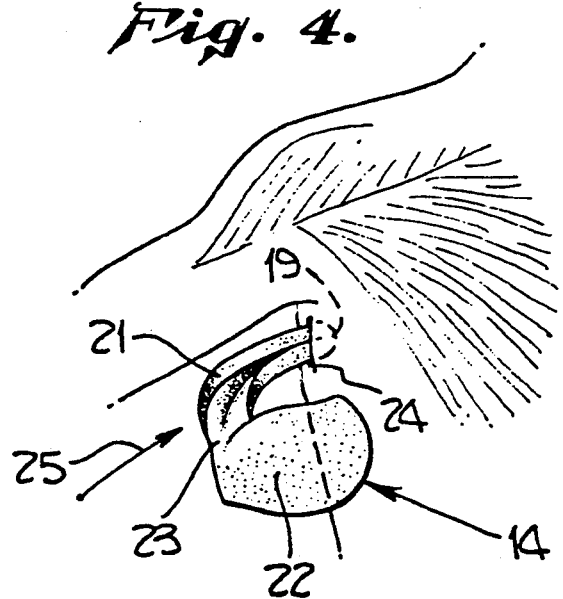
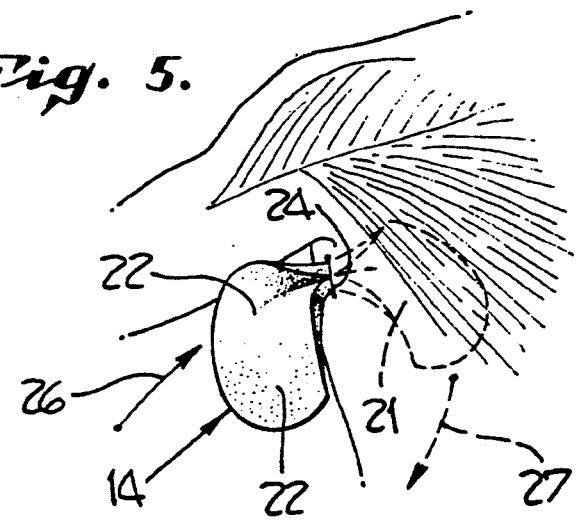
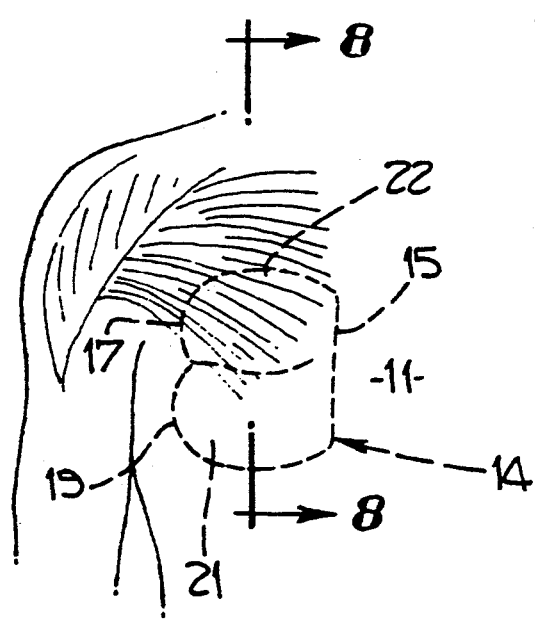
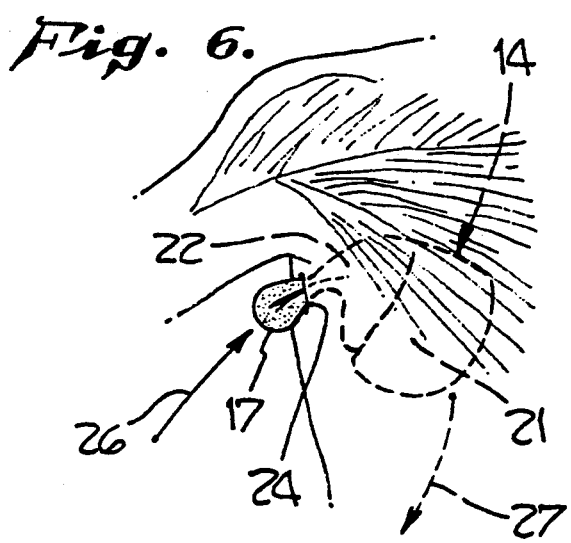

PECTORAL IMPLANT AND METHOD FOR IMPLANTING THE SAME

BACKGROUND OF THE INVENTION

1. Field of the Invention

The invention relates to body implants; and, more particularly, pectoral implants for men.

2. Description of the Prior Art

Breast implants for women have been known for many years. Such implants are generally made of a medical grade of silicon elastomer material. If a man wanted to build up his chest, he had to engage in strenuous exercises over a long period of time. It has been suggested that pectoral implants can be made to the chest of a male to build up various parts of the human body. One such article on chest and calf implants appeared in the Dec. 9, 1990 issue of the Los Angeles Times, magazine section, page 46. In this article, the insertion of six inch long tapered pieces of silicone into a slit in the armpit of a man is disclosed. The man's own tissue encapsulates the implants and holds them in place.

The article goes on to say that bodybuilders have used this technique to simulate a built-up body. Such chest implants can be used to build up one's chest where exercising is difficult or impossible. The applicant herein is discussed in the aforementioned article as providing one such individual with chest implants.

No prior art patent is known relating to chest implants and the method of implanting the same. In the implants discussed in the aforementioned article, three separate and independent pieces of implant material must be surgically installed and then "fanned out" to simulate the natural contours of the patient's chest. Thus, the pieces must be carefully aligned.

There is thus a need for a single chest implant and a method for implanting the same that can simulate the natural contours of a male chest.

SUMMARY OF THE INVENTION

It is an object of this invention to provide a pectoral implant for men.

It is a further object of this invention to provide a method for implanting a pectoral implant in a man.

It is still further an object of this invention to provide a single unitary piece of implant material that can be implanted in a male chest that follows the natural contours of the chest.

These and other objects are preferably accomplished by providing a pectoral implant of a soft silicone material that is contoured to the chest of a male. The implant is split partway therethrough so that it can be folded and inserted into a small slit under the armpit of a male and moved into the chest area to simulate the built-up chest appearance of the male.

BRIEF DESCRIPTION OF THE DRAWING

FIG. 1 is a vertical view of a male showing a normal chest with the muscles exposed;

FIG. 2 is a perspective view of a pectoral implant in accordance with the teachings of the invention;

FIG. 3 is an illustration of the first step in the method of implanting the implant of FIG. 2 in the male of FIG. 1;

FIGS. 4 to 7 are successive steps illustrating the implanting of the implant of FIG. 2;

FIG. 8 is a view taken along lines 8—8 of FIG. 7; and

FIG. 9 is a view similar to FIG. 1 showing pectoral implants in dotted lines as implanted in the male of FIG. 1.

DESCRIPTION OF THE PREFERRED EMBODIMENT

Referring now to FIG. 1 of the drawing, a male FIG. 10 is shown having a chest 11 showing a pectoralis minor muscle layer 12 and an underlying pectoralis major muscle layer 13. The chest 11 is shown sagging and, in FIG. 2, a chest implant 14 is shown prior to insertion into the chest 11 of the FIG. 10 shown in FIG. 1. As will be discussed further hereinbelow, and as seen in dotted lines in FIG. 9, two such implants 14 are shown implanted into the FIG. 10 in FIG. 9.

Implant 14, FIG. 2, is a unitary piece of a suitable implant material, such as silicone, having a slightly concave back wall 15, an integral curved side wall 16, which wall 16 curves around to a rounded first front wall portion 17, and an integral slightly concave side wall 18 which curves around to a rounded second front wall portion 19.

As seen in FIG. 2, wall portions 17, 19 intersect at a generally S-shaped curved line 20 which divides implant 14 into two sections 21, 22 and creates an inside edge on each section. As seen, line 20 does not extend to wall 15 and, as seen in FIGS. 3 to 7, allows implant 14 to be split apart or separated (yet hinged or attached to each other by an integral section 23—see FIG. 4) for easy insertion into the chest 11 of the FIG. 10, as will be discussed.

As seen in FIG. 8, implant 14 is rounded at walls 16, 18 and slightly arcuate or curved to conform to the chest cavity 24 in which implant 14 is inserted.

The installation of implant 14 will now be discussed with particular reference to FIGS. 3 to 7. The surgeon first makes a small incision in the armpit of the FIG. 10. As seen in FIG. 4, one of the sections of implant 14, such as section 21, is pulled away from section 22, folded about itself along its longitudinal axis (the resilient material allowing from such folding) and inserted through slit 24 in the direction of arrow 25, the rounded end 19 being inserted first.

As seen in FIG. 5, the surgeon continues to push implant 14 in the direction of arrow 26 until section 21 is inside the FIG. 10, and moving in the direction of arrow 27 (section 22 being outside of FIG. 5). Insertion is continued by folding section 22 along its longitudinal axis and pushing the same through slit 24 (see FIG. 6), rounded end 17 being the only part of implant 14 not inside of FIG. 6.

The implant 14 is moved by the surgeon into chest 11 until the implant 14 is in the position shown in FIG. 7 (the right implant being shown—the left implant being installed in like manner—see FIG. 9).

Thus, as seen in FIGS. 7 and 9, each implant 14 has its back wall 15 generally vertical and the rounded front wall portions 17, 19 extending outwardly and laterally from walls 15. As seen in FIG. 8, implant 14 is disposed in a pocket or cavity 24 formed between the muscle layers (outer skin 28 overlying outer layer 12).

It can be seen that section 23 forms a bend area for implant 14 allowing the sections 20, 21 to be split apart for insertion. The implant 14 is a sculptured silicone pad and both left and right implants 14 may be molded from the same mold. The desired dimensions for each insert is about 15 cms. wide by 17 cms. long by 2 cms. thick. The split line 20 may extend any suitable distance between parts 21, 22 as long as the implant 14 can be folded and inserted as heretofore stated.

It can be seen that there is disclosed a pectoral implant and method for implanting the same. The implant and method results in a natural appearing pectoral implant simulating the musculature chest of a male.

I claim:

1. A male chest implant comprising:
a unitary body of implant material having a slightly concave cross-section and being divided into a first section and a second section, each section having an inside edge and an outside edge, the inside edges of the first and second sections being adjacent one another with the first and second sections being attached to one another only at one end of the respective inside edge of each section.

2. In the implant of claim 1 wherein the overall shape of the implant is substantially rectangular and the inside edges of the first and second sections lie along a line substantially perpendicular to a back wall of the implant.

3. In the implant of claim 2, each section having a front wall spaced from the back wall, said front walls each being curved and intersection with respective ones of said inside edges.

4. In the implant of claim 1 wherein said inside edges of said first and second sections are generally S-shaped.

5. In the implant of claim 1 wherein said piece is about 15 cms. wide by 17 cms. long by 2 cms. thick.

6. In the implant of claim 1 wherein said implant is of a soft silicone material.

7. A method for implanting a pectoral implant in the chest of a male comprising the steps of:
providing a piece of soft silicone material having a first section separated from a second section by a cutting line extending partway through said piece;
making a small incision in the arm pit of said male;
folding said first section of said piece of material about itself along an axis generally parallel to said cutting line;
inserting a first end of said folded first section through said incision; moving said implant into said male until said second section is adjacent said incision;
folding said second section of said piece of material about itself along an axis generally parallel to said cutting line;
moving said second section through said incision until said entire piece of material is through said incision and within the body of said male;
moving said implant into the chest of said male between the pectoralis major muscle and the pectoralis minor muscle; and
subsequently fanning out said piece of material within said chest to simulate the natural contours of a male chest.

* * * * *